(12) United States Patent
Chen et al.

(10) Patent No.: US 12,055,038 B2
(45) Date of Patent: Aug. 6, 2024

(54) FLUID HOLDUP MONITORING IN DOWNHOLE FLUID SAMPLING TOOLS

(71) Applicant: Halliburton Energy Services, Inc., Houston, TX (US)

(72) Inventors: Zhonghuan Chen, Houston, TX (US); Bin Dai, Houston, TX (US); Christopher Michael Jones, Houston, TX (US); Wei Zhang, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 39 days.

(21) Appl. No.: 17/572,684

(22) Filed: Jan. 11, 2022

(65) Prior Publication Data

US 2023/0220771 A1    Jul. 13, 2023

(51) Int. Cl.
| | | |
|---|---|---|
| *E21B 49/08* | (2006.01) | |
| *G01N 9/32* | (2006.01) | |
| *G01N 21/3577* | (2014.01) | |
| *G01N 21/17* | (2006.01) | |

(52) U.S. Cl.
CPC ............ *E21B 49/081* (2013.01); *G01N 9/32* (2013.01); *G01N 21/3577* (2013.01); *G01N 2021/178* (2013.01)

(58) Field of Classification Search
CPC ..... E21B 49/081; E21B 49/0875; G01N 9/32; G01N 21/3577; G01N 2021/178
See application file for complete search history.

(56) References Cited

U.S. PATENT DOCUMENTS

| | | | |
|---|---|---|---|
| 5,361,632 A | 11/1994 | Magnani | |
| 5,631,413 A * | 5/1997 | Young | E21B 47/103 73/61.49 |
| 6,028,307 A * | 2/2000 | Young | E21B 47/113 250/269.3 |
| 7,408,645 B2 * | 8/2008 | DiFoggio | G02B 26/02 356/70 |
| 10,927,672 B2 | 2/2021 | Dai et al. | |
| 11,808,147 B2 * | 11/2023 | Chen | E21B 49/081 |
| 2006/0139646 A1 * | 6/2006 | DiFoggio | G01J 3/108 356/436 |
| 2010/0206063 A1 * | 8/2010 | Fujisawa | E21B 49/10 73/152.24 |
| 2012/0018152 A1 * | 1/2012 | Zuilekom | E21B 49/10 166/264 |
| 2014/0096957 A1 * | 4/2014 | van Zuilekom | E21B 43/12 166/250.01 |
| 2017/0198574 A1 | 7/2017 | Donzier et al. | |
| 2018/0245465 A1 * | 8/2018 | Khan | E21B 49/086 |
| 2021/0332699 A1 | 10/2021 | Dai et al. | |
| 2023/0220771 A1 * | 7/2023 | Chen | E21B 49/10 166/250.01 |

FOREIGN PATENT DOCUMENTS

| | | |
|---|---|---|
| CN | 202451148 | 9/2012 |
| WO | 2019-052235 | 4/2009 |

OTHER PUBLICATIONS

International Search Report and Written Opinion for Application No. PCT/US2022/011917, dated Sep. 27, 2022.

\* cited by examiner

*Primary Examiner* — John Fitzgerald
(74) *Attorney, Agent, or Firm* — John Wustenberg; C. Tumey Law Group PLLC

(57) ABSTRACT

Fluid holdups within a downhole sampling tool are identified by comparing high- and low-resolution measurements of fluid samples.

12 Claims, 6 Drawing Sheets

FLUID HOLDUP MONITORING IN DOWNHOLE FLUID SAMPLING TOOLS

FIELD OF THE INVENTION

The present invention relates generally to hydrocarbon exploration using fluid sampling tools and, more specifically, to methods and systems to monitor and mitigate fluid holdups within downhole sampling tools.

BACKGROUND

During formation tester pump-outs, reservoir fluids and mud fluids are mixed in the sampling probe, and flow through the fluid path for real time measurement and analysis. The sampled fluids can be single-phase solutions or multi-phase mixtures. In multiphase cases, the fluid may be discontinuous or continuous fluid phases including liquid-liquid (aqueous and or organic phases), liquid-gas, or liquid solid, or other types. As described herein, a fluid mixture of fluids and solids may be referred to as a fluid mixture. Multiphase fluid may be present in the formation or may be produced upon samplings such as the single-phase cases, which may also yield fluid droplets or gas bubbles as the pressure decreases or the temperature increases.

In field systems, the fluid droplets or gas bubbles may hold up on the wall of the pipe, tubing or tool, or be cleared by the flowing fluids. As to whether a fluid is cleared from a system depends complicatedly on the physical properties of all distinct phases of the mixture, and hence the pressure and temperature condition, and the flowing rates of the fluids, as well as the geometry of the flow system, and orientation of the flow and flow path with respect to gravity throughout the entire connected flow path. Moreover, the fluid path through the tool is not straight, but takes a few bends, and goes through valves which have a very tortuous geometry. The curvature and non-smoothness of the fluid pipe also provides environment for bubbles or droplets in the flow trapping therein. The physical properties over which the fluid holdup is dependent include, but are not limited to, surface tension, density, and viscosity with respect to the multiple phases. The flow path dependent properties include, but are not limited to, the flow path diameter, irregularities, dead volumes, bends and tortuous nature, and restrictions.

These holdups may be very problematic to some subsurface fluid measurements, and any further operations based on these measurements, as well as sampling and production. Such applications include formation testers, drill stem tests (DSTs), multilateral productions, horizontal production, and highly deviated production. Subsurface measurements include physical property measurements including density, pressure, temperature, capacitance, dielectric spectroscopy, viscosity, compressibility, speed of sound, and optical measurements including, but not limited to, optical spectroscopy, index of refraction, florescence, and coulometric measurements. Chemical measurements include pH, eH, and compositions such as, but not limited to, saturates, aromatics, resins, asphaltenes, C6+, methane, ethane, propane, butane, pentane, total acid number (TAN), Equation of State pseudo components and others. The embodiments herein are described with formation testers using optical measurements, but are not intended to be limited therein. Optical measurements are one of the measurements which are sensitive to the fluid holdups used herein as an example. Also used as an example is formation fluid sampling.

During the formation fluid sampling, the formation fluids are usually sampled until the fluid contamination becomes low enough to obtain or extrapolate representative formation fluid properties from that sample. The fluid ratio is estimated based on optical measurements and used for the contamination analysis. However, when there are holdups of any phase on the optical path, then that phase ratio estimation based on the observed optical data may be distorted. For example, if the formation fluid is held up in place then the contamination measurement by the optical means may be low even if the fractional flow rate of the contamination itself is still high. It may lead to unreliable sampling for the formation fluids.

As an example, when the problematic holdup is the mud fluid filtrate, then the dynamic observations on all optical channels may be affected by these holdups. It may become very difficult to extract any pure formation signature from the observed optical data. Moreover, the further fluid compositional analysis becomes unreliable, due to its highly dependency on the holdup fluid signatures.

In conventional approaches, a mechanical flushing procedure is usually designed to produce fluid from the formation against the pressure of the mud column. However, if the flow is multi-phase then one phase may be held up. A procedure may be used to clear the fluid from the holdup region. This procedure or others may be used in other systems such as production systems. To perform the flushing procedure, the exit valve to the flow line is first closed to allow pressure to build (e.g., 4,000 psi-8,000 psi of pressure) in the tool while continuing to pump. This compresses the fluid substantially. Then, the exit valve to the flow line is suddenly opened and the pressure is released which results in the fluid trapped over the 15 meters to 40 meters suddenly expanding and the trapped fluid is jarred free. Without any information on whether there is or is not trapped holdups in the subsurface, the mechanical flushing procedure is usually done periodically. However, currently there is no assurance the fluid holdups are cleared completely after the procedure, nor whether the subsequent measurements or sampling are reliable. The periodical flushing may also be applied too early when no holdups appeared or too late after the holdups has affected the measurements.

DESCRIPTION OF ILLUSTRATIVE EMBODIMENTS

Figure 1:
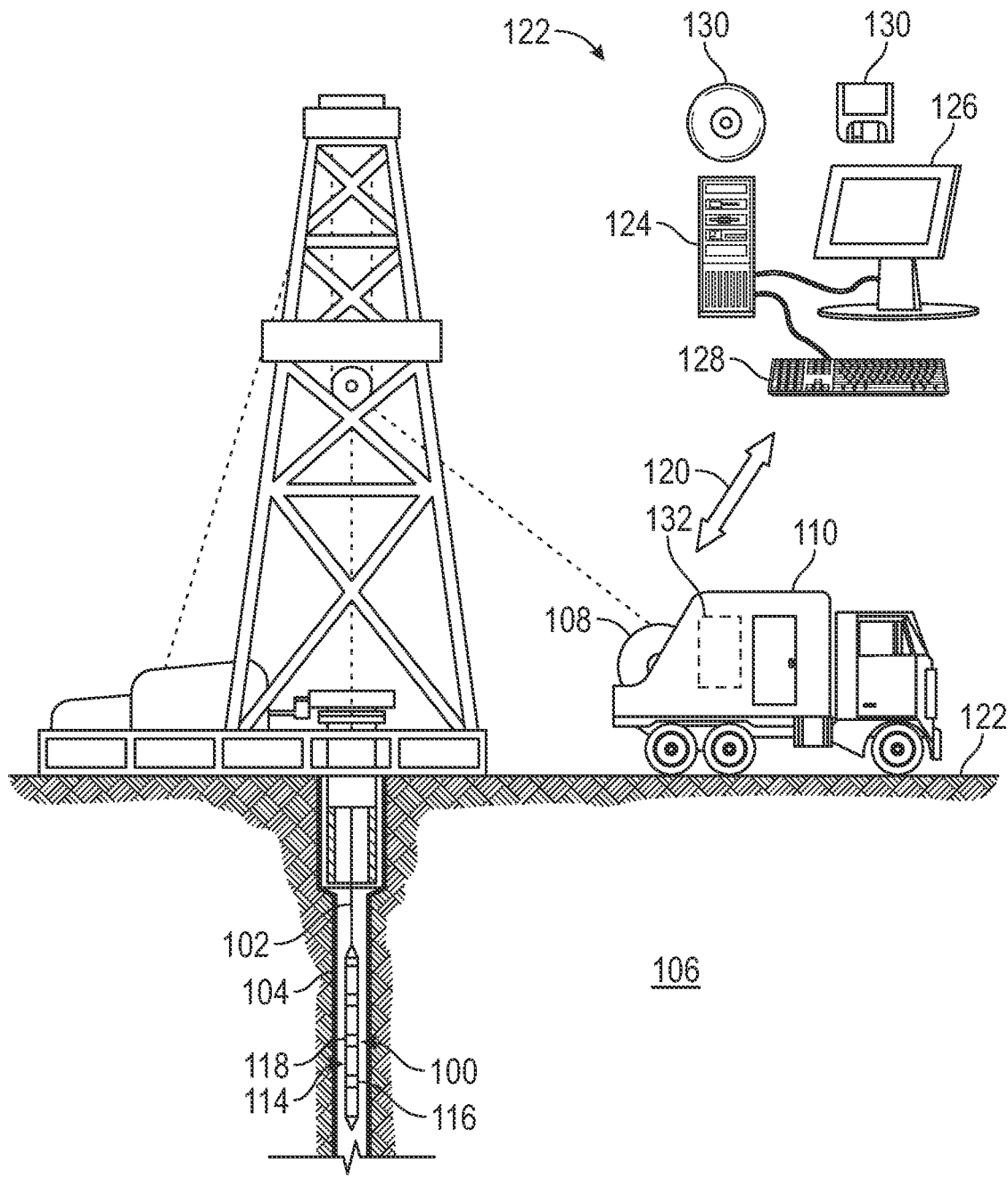
FIG. 1 is a schematic diagram of downhole fluid sampling tool on a wireline conveyance, according to certain illustrative embodiments of the present disclosure.

Illustrative embodiments and related methods of the present disclosure are described below as they might be employed to monitor, identify and mitigate fluid holdups in downhole fluid sampling operations. In the interest of clarity, not all features of an actual implementation or methodology are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methodologies of the invention will become apparent from consideration of the following description and drawings.

Exemplary embodiments of the present invention are directed to systems and methods to identify and mitigate fluid holdups in downhole fluid sampling operations. As mentioned above, during sampling and measurement operations using reservoir description tools (i.e., sampling tools), the fluids may be trapped on the wall of the sampling path. These trapped fluid holdups reduce the reliability of sampling and the accuracy of fluid measurements such as (physical measurements: density, pressure, temperature, capacitance, dielectric spectroscopy, viscosity, compressibility, speed of sound, and optical measurement including, but not limited to, optical spectroscopy, index of refraction, florescence, and coulometric measurements. Chemical measurements include pH, eH, and other compositions such as, but not limited to, saturates, aromatics, resins, asphaltenes, C6+, methane, ethane, propane, butane, pentane, total acid number (TAN), Equation of State pseudo components and others) or rock fluid properties such as mobility. In other systems, the holdup may degrade production.

This present disclosure proposes an approach to monitor the fluid holdups. The illustrative methods are based on the discovery that physical measurements of different spatial (space) and/or temporal (time) resolutions may have different sensitivities to the fluid holdups. A high or low spatial resolution is categorized with respect to a high or low temporal resolution of that measurement and the spatial distribution and temporal rate of oscillations of the various phases for a measurement sensitive to that phase. A low spatial resolution measurement will measure a composite signal from multiple phases within the temporal resolution of the measurement. In some cases, the temporal resolution of the measurement may be altered by stacking signals, integrating signals or increasing the analogue to digital conversion rate of the signals. Some measurements may also have adjustable spatial measurements, especially with the combination of sensor arrays or pseudo sensor arrays from multiple sensor types.

A lower temporal measurement may also adjust the categorization of a spatial measurement of the same dimensions as high or low resolution. For instance, a high spatial resolution measurement may be high with respect to the temporal resolution if the temporal resolution also is sufficiently high. However, if the temporal resolution is not sufficiently high, then then spatial resolution may be recategorized as low resolution.

Further, the resolution is defined with respect to the phase distribution such that for instance, if the distribution is a long slug flow (meaning there are long periods of single phase for the sensor to observe), then the resolution of a measurement may be high. However, if the spatial distribution is a short slug flow (meaning a short periods of slugs for the sensor to observe), then the same sensor configuration and temporal measurement may be low resolution. Also, if the rate of oscillation may be defined not only by the distribution of the slugs, but also by the temporal rate of the slugs such that if they are passing through the observation region of the sensor fast, then the measurement may be of a low temporal resolution, but if they are passing through the observation region of the sensor slowly then the measurement may be of high temporal resolution.

The effect of high-resolution vs low resolution is determined by the nature of the composite signal, and whether the individual phases may be resolved (i.e., means the system can distinguish the fluids with or without droplets and bubbles). If the phases cannot be resolved, the measurement is of low resolution and, if they may be resolved, then the measurement is of high resolution. The measurement may be considered higher resolution vs. another measurement if the composite signal may be better resolved with respect to a specific phase. Of course, since some sensor measurements may not have the same sensitivity to each phase, then the degree of high to low resolution for a measurement may be different for the same system for two different phases of the measurement. Also, there are many different types of multiphase flow, such that the degree of oscillation is also dependent on the nature of that flow. There may be one or more or no continuous phases of a multiphase flow. The flow may take slug flow, dispersed flow or split flow forms. The flow may be a dispersion or an emulsion. A variety of other possible multiphase flow forms may also be utilized.

In view of the foregoing, this disclosure utilizes high spatial resolution sensors to obtain the high spatial resolution measurements, and low spatial resolution sensors to obtain the low spatial resolution measurements. Examples of high spatial resolution sensors can be but not limited to optical, infrared or laser sensors. Examples of low spatial resolution sensors can be but not limited to density or capacitance sensors.

This disclosure proposes to estimate two mud filtrate fluid ratios independently from multi-physical measurements, and to compare the mud fluid ratios to enable monitoring of trapped fluid holdups. The illustrative methods described herein can then be used as a real-time reliability quality check for fluid sampling and measurement, and also provide guide information for field engineers to apply the mechanical flushing procedure.

In a generalized method of the present disclosure, methods to identify fluid holdups in multiple systems for downhole fluid sampling operations are presented. A sampling tool positioned along a wellbore is used to obtain one or more fluid measurements having a high spatial resolution. The sampling tool is also used to obtain more fluid measurements having a low spatial resolution. A ratio is calculated for the high-resolution fluid measurement. A ratio is also calculated for the low-resolution fluid measurement. The ratios of the high- and low-resolution measurements are compared and, based upon this comparison, fluid holdups within the sampling tool are identified. Thereafter, a flushing procedure may be conducted in order to clear the holdup(s).

FIG. 1 is a schematic diagram of downhole fluid sampling tool 100 on a conveyance 102. As illustrated, wellbore 104 may extend through subterranean formation 106. In examples, reservoir fluid may be contaminated with well fluid (e.g., drilling fluid) from wellbore 104. As described herein, the fluid sample may be analyzed to determine fluid contamination and other fluid properties of the reservoir fluid. As illustrated, a wellbore 104 may extend through subterranean formation 106. While the wellbore 104 is shown extending generally vertically into the subterranean formation 106, the principles described herein are also applicable to wellbores that extend at an angle through the subterranean formation 106, such as horizontal and slanted wellbores. For example, although FIG. 1 shows a vertical or low inclination angle well, high inclination angle or horizontal placement of the well and equipment is also possible. It should further be noted that while FIG. 1 generally depicts a land-based operation, those skilled in the art will readily recognize that the principles described herein are equally applicable to subsea operations that employ floating or sea-based platforms and rigs, without departing from the scope of the disclosure.

As illustrated, a hoist 108 may be used to run downhole fluid sampling tool 100 into wellbore 104. Hoist 108 may be disposed on a vehicle 110. Hoist 108 may be used, for example, to raise and lower conveyance 102 in wellbore 104. While hoist 108 is shown on vehicle 110, it should be understood that conveyance 102 may alternatively be disposed from a hoist 108 that is installed at surface 112 instead of being located on vehicle 110. Downhole fluid sampling tool 100 may be suspended in wellbore 104 on conveyance 102. Other conveyance types may be used for conveying downhole fluid sampling tool 100 into wellbore 104, including coiled tubing and wired drill pipe, conventional drill pipe for example. Downhole fluid sampling tool 100 may comprise a tool body 114, which may be elongated as shown on FIG. 1.

Tool body 114 may be any suitable material, including without limitation titanium, stainless steel, alloys, plastic, combinations thereof, and the like. Downhole fluid sampling tool 100 may further include one or more sensors 116 for measuring properties of the fluid sample, reservoir fluid, wellbore 104, subterranean formation 106, or the like. In examples, downhole fluid sampling tool 100 may also include a fluid analysis module 118, which may be operable to process information regarding fluid sample, as described below. The downhole fluid sampling tool 100 may be used to collect fluid samples from subterranean formation 106 and may obtain and separately store different fluid samples from subterranean formation 106.

In certain illustrative embodiments, fluid analysis module 118 may comprise at least one sensor that may continuously monitor a reservoir fluid. Such sensors include optical sensors, acoustic sensors, electromagnetic sensors, conductivity sensors, resistivity sensors, selective electrodes, density sensors, capacitance sensors, mass sensors, thermal sensors, chromatography sensors, viscosity sensors, bubble point sensors, fluid compressibility sensors, flow rate sensors. Sensors may measure a contrast or an oscillating ratio between drilling fluid mud or filtrate properties and formation fluid properties, also referred to an oil-water ratios or formation fluid ratios. Fluid analysis module 118 may be operable to derive properties and characterize the fluid sample. By way of example, fluid analysis module 118 may measure absorption, transmittance, or reflectance spectra and translate such measurements into component concentrations of the fluid sample, which may be lumped component concentrations. The fluid analysis module 118 may also measure gas-to-oil ratio, fluid composition, water cut, live fluid density, live fluid viscosity, formation pressure, and formation temperature.

Fluid analysis module 118 may also be operable to determine fluid contamination of the fluid sample and may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, fluid analysis module 118 may include random access memory (RAM), one or more processing units, such as a central processing unit (CPU), or hardware or software control logic, ROM, and/or other types of nonvolatile memory.

Any suitable technique may be used for transmitting data signals from the downhole fluid sampling tool 100 to the surface 112. As illustrated, a communication link 120 (which may be wired or wireless, for example) may be provided that may transmit data from downhole fluid sampling tool 100 to an information handling system 122 at surface 112. Information handling system 122 may include a processing unit 124, a monitor 126, an input device 128 (e.g., keyboard, mouse, etc.), and/or computer media 130 (e.g., optical disks, magnetic disks) that can store code representative of the methods described herein. The information handling system 122 may act as a data acquisition system and possibly a data processing system that analyzes information from downhole fluid sampling tool 100. For example, information handling system 122 may process the information from downhole fluid sampling tool 100 for determination of fluid contamination or fluid holdups as described herein.

The information handling system 122 may also determine additional properties of the fluid sample (or reservoir fluid), such as component concentrations, pressure-volume-temperature properties (e.g., bubble point, phase envelop prediction, etc.) based on the fluid characterization. This processing may occur at surface 112 in real-time. Alternatively, the processing may occur downhole hole or at surface 112 or another location after recovery of downhole fluid sampling tool 100 from wellbore 104. Alternatively, the processing may be performed by an information handling system in wellbore 104, such as fluid analysis module 118. The resultant fluid contamination, fluid holdups and/or fluid properties may then be transmitted to surface 112, for example, in real-time.

Figure 2:
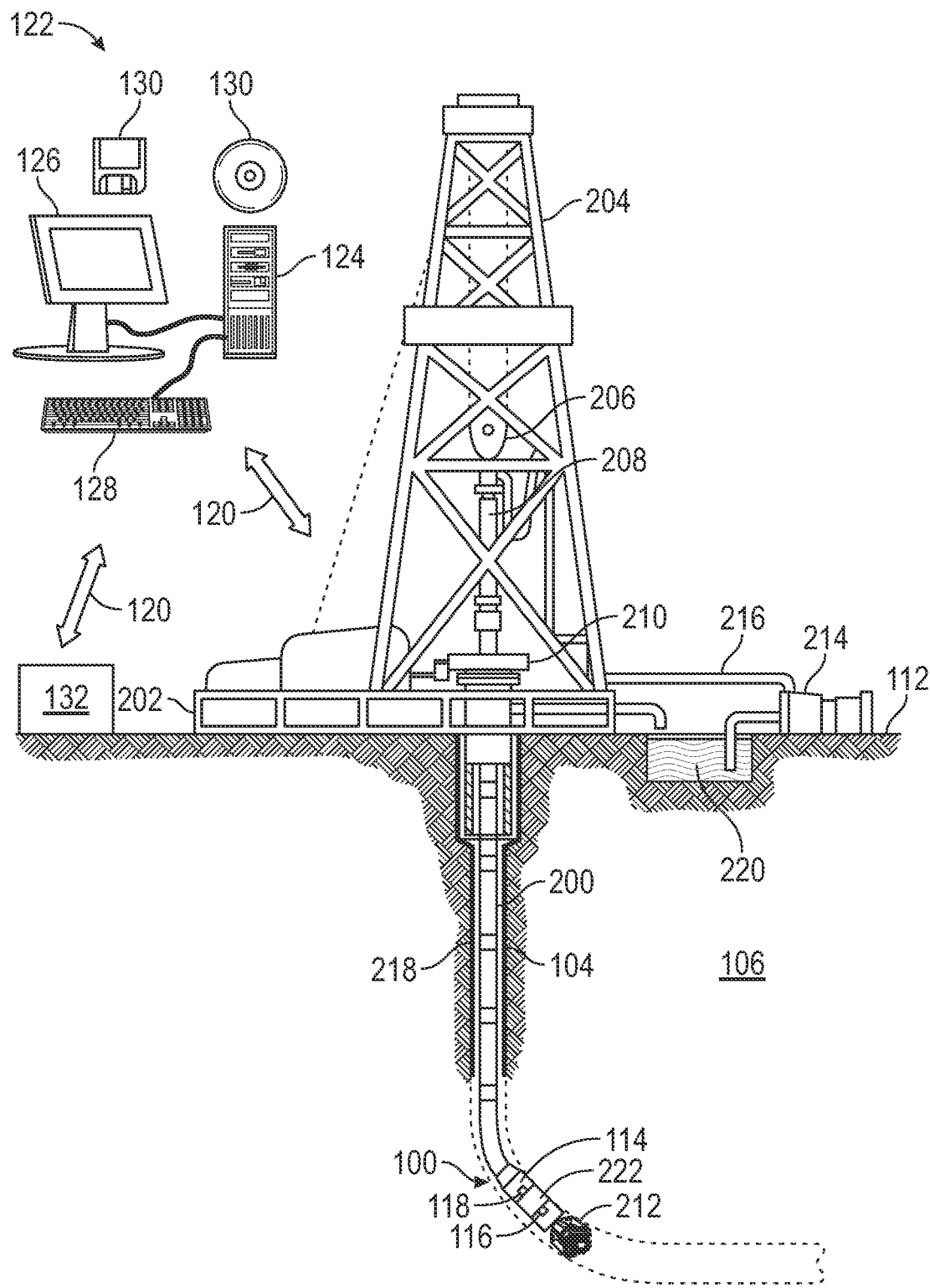
FIG. 2 is a schematic diagram of downhole fluid sampling tool disposed on a drill string in a drilling operation, according to certain illustrative embodiments of the present disclosure.

Referring now to FIG. 2, a schematic diagram of downhole fluid sampling tool 100 disposed on a drill string 200 in a drilling operation. Downhole fluid sampling tool 100 may be used to obtain a fluid sample, for example, a fluid sample of a reservoir fluid from subterranean formation 106. The reservoir fluid may be contaminated with wellbore fluid such (e.g., drilling fluid filtrate) from wellbore 104. As described herein, the fluid sample may be analyzed to determine fluid contamination, fluid holdups and/or fluid properties of the reservoir fluid. As illustrated, a wellbore 104 may extend through subterranean formation 106. While the wellbore 104 is shown extending generally vertically into the subterranean formation 106, the principles described herein are also applicable to wellbores that extend at an angle through the subterranean formation 106, such as horizontal and slanted wellbores. For example, although FIG. 2 shows a vertical or low inclination angle well, high inclination angle or horizontal placement of the well and equipment is also possible. It should further be noted that while FIG. 2 generally depicts a land-based operation, those ordinarily skilled in the art will readily recognize that the principles described herein are equally applicable to subsea operations that employ floating or sea-based platforms and rigs, without departing from the scope of the disclosure.

As illustrated, a drilling platform 202 may support a derrick 204 having a traveling block 206 for raising and lowering drill string 200. Drill string 200 may include, but is not limited to, drill pipe and coiled tubing, as generally known to those skilled in the art. A kelly 208 may support drill string 200 as it may be lowered through a rotary table 210. A drill bit 212 may be attached to the distal end of drill string 200 and may be driven either by a downhole motor and/or via rotation of drill string 200 from the surface 112. Without limitation, drill bit 212 may include, roller cone bits, PDC bits, natural diamond bits, any hole openers, reamers, coring bits, and the like. As drill bit 212 rotates, it may create and extend wellbore 104 that penetrates various subterranean formations 106. A pump 214 may circulate drilling fluid through a feed pipe 216 to kelly 208, downhole through interior of drill string 200, through orifices in drill bit 212, back to surface 112 via annulus 218 surrounding drill string 200, and into a retention pit 220.

Drill bit 212 may be just one piece of a downhole assembly that may include one or more drill collars 222 and downhole fluid sampling tool 100. Downhole fluid sampling tool 100, which may be built into the drill collars 222 may gather measurements and fluid samples as described herein. One or more of the drill collars 222 may form a tool body 114, which may be elongated as shown on FIG. 2. Tool body 114 may be any suitable material, including without limitation titanium, stainless steel, alloys, plastic, combinations thereof, and the like. Downhole fluid sampling tool 100 may be similar in configuration and operation to downhole fluid sampling tool 100 shown on FIG. 1 except that FIG. 2 shows downhole fluid sampling tool 100 disposed on drill string 200. Alternatively, the sampling tool may be lowered into the wellbore after drilling operations on a wireline.

Downhole fluid sampling tool 100 may further include one or more sensors 116 for measuring properties of the fluid sample reservoir fluid, wellbore 104, subterranean formation 106, or the like. The properties of the fluid are measured as the fluid passes from the formation through the tool passageways and into either the wellbore or a sample container. As fluid is flushed in the near wellbore region by the mechanical pump, the fluid that passes through the tool generally reduces in drilling fluid filtrate content, and generally increases in formation fluid content. The downhole fluid sampling tool 100 may be used to collect a fluid sample from subterranean formation 106 when the filtrate content has been determined to be sufficiently low. Sufficiently low depends on the purpose of sampling. For some laboratory testing below 10% drilling fluid contamination is sufficiently low, and for other testing below 1% drilling fluid filtrate contamination is sufficiently low. Sufficiently low also depends on the nature of the formation fluid such that lower requirements are generally needed, the lighter the oil as designated with either a higher GOR or a higher API gravity. Sufficiently low also depends on the rate of cleanup in a cost benefit analysis since longer pumpout times required to incrementally reduce the contamination levels may have prohibitively large costs.

The fluid sample may comprise a reservoir fluid, which may be contaminated with a drilling fluid or drilling fluid filtrate. Downhole fluid sampling tool 100 may obtain and separately store different fluid samples from subterranean formation 106 with fluid analysis module 118. Fluid analysis module 118 may operate and function in the same manner as described above. However, storing of the fluid samples in the downhole fluid sampling tool 100 may be based on the determination of the fluid contamination. For example, if the fluid contamination exceeds a tolerance, then the fluid sample may not be desired to be stored. If the fluid contamination is within a tolerance, then the fluid sample may be stored in the downhole fluid sampling tool 100.

As previously described, information from downhole fluid sampling tool 100 may be transmitted to an information handling system 122, which may be located at surface 112. As illustrated, communication link 120 (which may be wired or wireless, for example) may be provided that may transmit data from downhole fluid sampling tool 100 to an information handling system 111 at surface 112. Information handling system 140 may include a processing unit 124, a monitor 126, an input device 128 (e.g., keyboard, mouse, etc.), and/or computer media 130 (e.g., optical disks, magnetic disks) that may store code representative of the methods described herein. In addition to, or in place of processing at surface 112, processing may occur downhole (e.g., fluid analysis module 118). In examples, information handling system 122 may perform computations as required herein.

Figure 3:
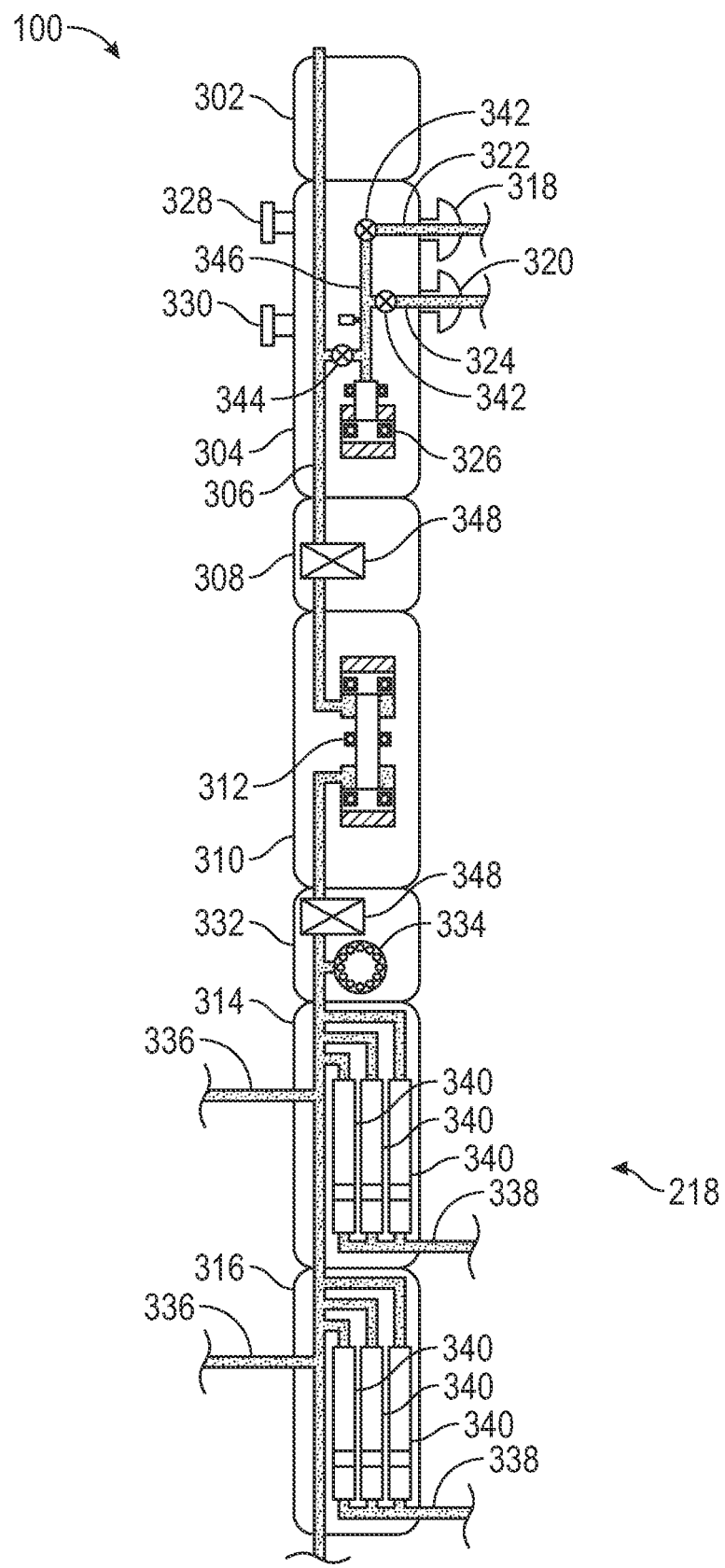
FIG. 3 is a schematic of downhole fluid sampling tool, according to certain illustrative embodiments of the present disclosure.

FIG. 3 is a schematic of downhole fluid sampling tool 100. In examples one embodiment, the downhole fluid sampling tool 100 includes a power telemetry section 302 through which the tool communicates with other actuators and sensors 116 in drill string 200 or conveyance 102 (e.g., referring to FIGS. 1 and 2), the drill string's telemetry section 302, and/or directly with a surface telemetry system (not illustrated). In examples, power telemetry section 302 may also be a port through which the various actuators (e.g., valves) and sensors (e.g., optical, infrared or laser sensors) in the downhole fluid sampling tool 100 may be controlled and monitored. In examples, power telemetry section 302 includes a computer that exercises the control and monitoring function. In one embodiment, the control and monitoring function is performed by a computer in another part of the drill string or wireline tool (not shown) or by information handling system 122 on surface 112 (e.g., referring to FIGS. 1 and 2).

In examples, downhole fluid sampling tool 100 includes a dual probe section 304, which extracts fluid from the reservoir and delivers it to a passageway 306 that extends from one end of downhole fluid sampling tool 100 to the other. Without limitation, dual probe section 304 includes two probes 318, 320 which may extend from downhole fluid sampling tool 100 and press against the inner wall of wellbore 104 (e.g., referring to FIG. 1). Probe channels 322, 324 may connect probes 318, 320 to passageway 306. The high-volume bidirectional pump 312 may be used to pump fluids from the reservoir, through probe channels 322, 324 and to passageway 306. Alternatively, a low volume pump 326 may be used for this purpose. Two standoffs or stabilizers 328, 330 hold downhole fluid sampling tool 100 in place as probes 318, 320 press against the wall of wellbore 104. In examples, probes 318, 320 and stabilizers 328, 330 may be retracted when downhole fluid sampling tool 100 may be in motion and probes 318, 320 and stabilizers 328, 330 may be extended to sample the formation fluids at any suitable location in wellbore 104. Other probe sections include focused sampling probes, oval probes, or packers.

In examples, passageway 306 may be connected to other tools disposed on drill string 200 or conveyance 102 (e.g., referring to FIGS. 1 and 2). In examples, downhole fluid sampling tool 100 may also include a quartz gauge section 308, which may include sensors to allow measurement of properties, such as temperature and pressure, of fluid in passageway 306. Additionally, downhole fluid sampling tool 100 may include a flow-control pump-out section 310, which may include a high-volume bidirectional pump 312 for pumping fluid through passageway 306. In examples, downhole fluid sampling tool 100 may include two multi-chamber sections 314, 316, referred to collectively as multi-chamber sections 314, 316 or individually as first multi-chamber section 314 and second multi-chamber section 316, respectively.

In examples, multi-chamber sections 314, 316 may be separated from flow-control pump-out section 310 by sensor section 332, which may house at least one non-optical fluid sensor 348 and/or at least optical measurement tool 334. It should be noted that non-optical fluid sensor 348 and optical measurement tool 334 (e.g., optical, infrared or laser sensors index of refraction, florescence, absorption, coulometric, visible, ultra-violate) may be disposed in any order on passageway 306. Additionally, although depicted in sensor section 332, both non-optical fluid sensor 348 (also referred to herein as a low spatial resolution sensor) and optical measurement sensor 334 (also referred to here as a high spatial resolution sensor) may be disposed along passageway 306 at any suitable location within downhole fluid sampling tool 100.

Further, non-optical fluid sensor 348 may be displaced within sensor section 332 in-line with passageway 306 to be a "flow through" sensor. In alternate examples, non-optical fluid sensor 348 may be connected to passageway 306 via an offshoot of passageway 306. Without limitation, non-optical measurement tool 348 may include but not limited to the density sensor, capacitance sensor, resistivity sensor, chromatography sensors, microfluidic sensors and/or combinations thereof. In examples, non-optical fluid sensor 348 may operate and/or function to identify fluid holdups or measure properties of drilling fluid filtrate.

Optical measurement tool 334 may be displaced within sensor section 332 in-line with passageway 306 to be a "flow through" sensor. In alternate examples, optical measurement tool 334 may be connected to passageway 306 via an offshoot of passageway 306. Without limitation, optical measurement tool 334 may include optical sensors, infrared sensors, laser sensors, acoustic sensors, electromagnetic sensors, conductivity sensors, resistivity sensors, selective electrodes, density sensors, mass sensors, thermal sensors, chromatography sensors, viscosity sensors, bubble point sensors, fluid compressibility sensors, flow rate sensors, microfluidic sensors, selective electrodes such as ion selective electrodes, and/or combinations thereof. In examples, optical measurement tool 334 may operate and/or function to identify fluid holdups or measure drilling fluid filtrate, discussed further below.

Additionally, multi-chamber section 314, 316 may comprise access channel 336 and chamber access channel 338. Without limitation, access channel 336 and chamber access channel 338 may operate and function to either allow a solids-containing fluid (e.g., mud) disposed in wellbore 104 in or provide a path for removing fluid from downhole fluid sampling tool 100 into wellbore 104. As illustrated, multi-chamber section 314, 316 may comprise a plurality of chambers 340. Chambers 340 may be sampling chamber that may be used to sample wellbore fluids, formation fluids, and/or the like during measurement operations.

During downhole measurement operations, a pumpout operation may be performed. A pumpout may be an operation where at least a portion of a fluid which may contain solids—(e.g., drilling fluid, mud, filtrate etc.) may move through downhole fluid sampling tool 100 until substantially increasing concentrations of formation fluids enter downhole fluid sampling tool 100. For example, during pumpout operations, probes 318, 320 may be pressed against the inner wall of wellbore 104 (e.g., referring to FIG. 1). Pressure may increase at probes 318, 320 due to compression against the formation 106 (e.g., referring to FIG. 1 or 2) exerting pressure on probes 318, 320. As pressure rises and reaches a predetermined pressure, valves 342 opens so as to close equalizer valve 344, thereby isolating fluid passageway 346 from the annulus 218. In this manner, valve 342 ensures that equalizer valve 344 closes only after probes 318, 320 has entered contact with mud cake (not illustrated) that is disposed against the inner wall of wellbore 104. In examples, as probes 318, 320 are pressed against the inner wall of wellbore 104, the pressure rises and closes the equalizer valve in fluid passageway 346, thereby isolating the fluid passageway 346 from the annulus 218. In this manner, the equalizer valve in fluid passageway 346 may close before probes 318, 320 may have entered contact with the mud cake that lines the inner wall of wellbore 104. Fluid passageway 346, now closed to annulus 218, is in fluid communication with low volume pump 326.

As low volume pump 326 is actuated, formation fluid may thus be drawn through probe channels 322, 324 and probes 318, 320. The movement of low volume pump 326 lowers the pressure in fluid passageway 346 to a pressure below the formation pressure, such that formation fluid is drawn through probe channels 322, 324 and probes 318, 320 and into fluid passageway 346. Probes 318, 320 serves as a seal to prevent annular fluids from entering fluid passageway 346. Such an operation as described may take place before, after, during or as part of a sampling operation.

Next, high-volume bidirectional pump 312 activates and equalizer valve 344 is opened. This allows for formation fluid to move toward high-volume bidirectional pump 312 through passageway 306. Formation fluid moves through passageway 306 to sensor section 332. Once the drilling fluid filtrate has moved into sensor section 332 high-volume bidirectional pump 312 may stop. This may allow the drilling fluid filtrate to be measured by optical measurement tool 334 within sensor section 332. Without limitation, any suitable properties of the formation fluid may be measured. Other pumps may be used such as centrifugal pumps, siphon pumps, or even underbalanced actuation of natural fluid flow such as but not limited to drill stem testing operations or underbalanced drilling operations, or managed pressure operations.

As mentioned previously, the present disclosure is primarily concerned with the identification of fluid holdups along the passageways of the fluid sampling tools, such as tool 100. In this regard, note the subsurface formation fluids are always mixtures of complicated chemical compositions, including water, alkanes (such as methane, ethane in gas or pentane, hexane in light oil), cycloalkanes, aromatics, asphaltic hydrocarbons (mainly in heavy oil) and some other organic compounds contain nitrogen, oxygen and sulfur. During the subsurface fluid sampling or measurement experiments, the formation fluids are pumped out as described above, and mixed with the mud filtrate fluids in different scales, which yields a multiphase fluid flow in the sampling probe. The multiphase fluid flow could be of different flow regimes in the fluid path. It may be the dispersed bubble flow with light gas bubbles or small fluid droplets suspended in the continuous fluid. It may also be the plug/slug flow, in which, the small bubbles or droplets merge together and yield larger bubbles or droplets of a bullet shape. The process of yielding fluid bubbles or droplets in the multiphase flow is highly complicated, depends on the fluid properties (see above) themselves and the pressure and temperature condition. Moreover, gas bubbles and fluid droplets can appear together, and there may also be bubbles or droplets of different compounds simultaneously in the fluid flow. There may be one or more continuous or discontinuous phases.

The fluid path (e.g., passageway 306) is not always straight, and the wall of the pipe is not smooth everywhere. When the multiphase fluids flow through these places, some of the fluid bubbles or droplets may hold up on the wall of the fluid pipe. The process of fluid holdup depends on the composition of the bubbles and droplets in the fluid flow and the properties of the fluid pipe materials. Methane, ethane bubbles may be easily stay on the wall of lipophilic pipe, while water droplets may stay on the hydrophile pipe. Moreover, when the fluids flow slow, a gas bubble or fluid droplet holding up on the wall may merge with other gas bubbles or fluid droplets; while when the fluids flow faster, these bubbles or droplets may be flushed away by the following flow.

Gas bubbles and fluid droplets may locate all along the fluid path. When they appear at the position of the optical ray path, they may lead to significant interference to the optical measurements and any following analysis or judgements based on these measurements. To improve the accuracy and reliability of the measurements, a flushing operation is needed to clear the holdups on the fluid path periodically. The flushing operation mechanically pumps some high-pressure fluids into the fluid pipe. The high-pressure and high flow rate fluid can clean all the holdups on the fluid path; however, unnecessary flushing procedures also pause the normal measurements and costs time to sample the formation fluids after the flushing.

Accordingly, in this disclosure, various illustrative embodiments propose methods to monitor the fluids holdups on the flow pipe. The monitoring information can be used as (a) an additional information to evaluate the accuracy and reliability of the measurements; and (b) a guide information for the mechanical flushing operation.

First, we begin with a discussion of measurement sensitivity vs. spatial resolution. The illustrative methods described herein are based on the discovery that different measurements on the fluids have different sensitivities to the fluid holdups on the pipe wall. In the subsurface measurements, the optical absorbance spectra are measured based on or approximated by the Beer-Lambert Law:

$$A(\lambda) = \eta \sum_k c_k \epsilon_k(\lambda), \qquad \text{Eq. 1}$$

where η is the length of the optical path in the fluid sample, c are concentrations of fluid compositions, and ε are the absorbance coefficients of related compositions. Nonlinear deviations from the Beer Lambert law may be modeled using nonlinear calibrations, or piecewise calibrations. Yet other optical methods such as florescence optical measurements are governed by other molecular or atomic state transition physics. Scattering measurements may be governed by linear approximations in dilute systems which may be highly nonlinear in slightly concentrated systems. The light ray source in the optical measurement is highly focused (compared to the diameters of most gas bubbles and fluid droplets), which makes the optical measurements very sensitive to the bubbles or droplets on its ray path (leading to abnormally high concentrations for the droplets fluids). This phenomenon is referred to as a high spatial resolution measurement.

On the other hand, some measurements are based on the integral effects of the physical properties over an area or a cube of fluid samples. These are low spatial resolution measurements. For example, the capacitance measurement is based on the electrical property with fluids of a specific area and the density measurement is based on the mass of a small fluid cube. To improve the accuracy of the electrical property or the mass, the area or volume for fluid sampling cannot be as small as the diameters of most of the gas bubbles and fluid droplets. In this case, the electrical and mass measurements are the integral effects of all the fluids in the sampling area or cube. It doesn't affect the integral effects whether the gas bubbles or fluid droplets are floating in the dominating fluid or holding up on the wall. In other words, these integral based measurements with low spatial resolution are not so sensitive to the gas bubbles and fluid droplets holdup.

Figure 4:
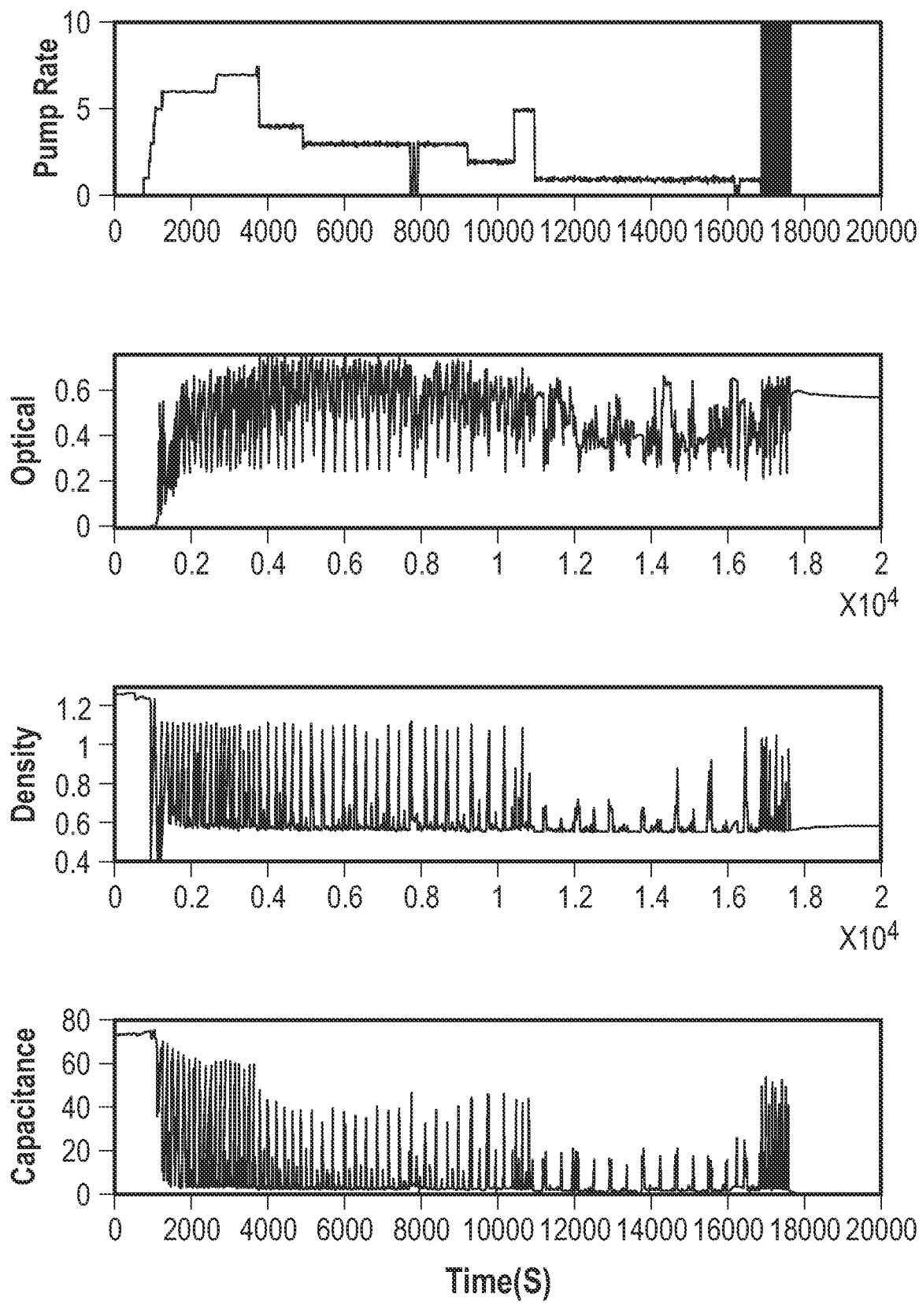
FIG. 4 are graphs which present some physical measurements in a subsurface fluid sampling experiment.

To verify this theory, FIG. 4 are graphs which present some physical measurements in a common subsurface fluid sampling experiment. During the sampling process, the tool pump starts at a high rate, and all the measurements including optical, density and capacitance are reasonable at first. After about 11000 seconds, the pump rate went down (the sampled fluids were mostly formation hydrocarbons). However, mud fluids (mainly water) start to hold up on the pipe wall due to the low pump rates and low flow rates. A periodical mechanical flushing procedure was applied at about 17000 s to clear the holdups on the sampling path. During the low-rate pumping, the density and capacitance measurements matched well with the fluids (low density and low capacitance dominated by formation hydrocarbons, with not much effect by the mud water holdups), while the optical measurements became unreliable (low optical transmittance on this channel indicating a high water-ratio). Accordingly, the measurement of a higher spatial resolution is more sensitive to the fluid holdups, while measurements of a low spatial resolution are not so sensitive.

Based on the foregoing discovery, the present disclosure estimates water ratios of the fluid samples using information derived from different measurements techniques. In the case there are no water holdups, the water ratios estimated from high-spatial resolution measurements (e.g., optical measurements) and low-spatial resolution measurements (e.g., density or capacitance measurements) should be consistent. However, when there are water holdups, the water ratio estimation based on high-resolution measurements will be much higher compared to the estimation based on low-resolution measurements. By comparing the two water ratio estimations, illustrative embodiments of the present disclosure allow monitoring of the water holdups in the subsurface device. Note the water ratio is the mud fluid ratio when the mud is water-based mud. Since the combination of the mud fluid ratio and the formation fluid ratio equals to one, estimating either of the two works for the monitoring.

Figure 5:
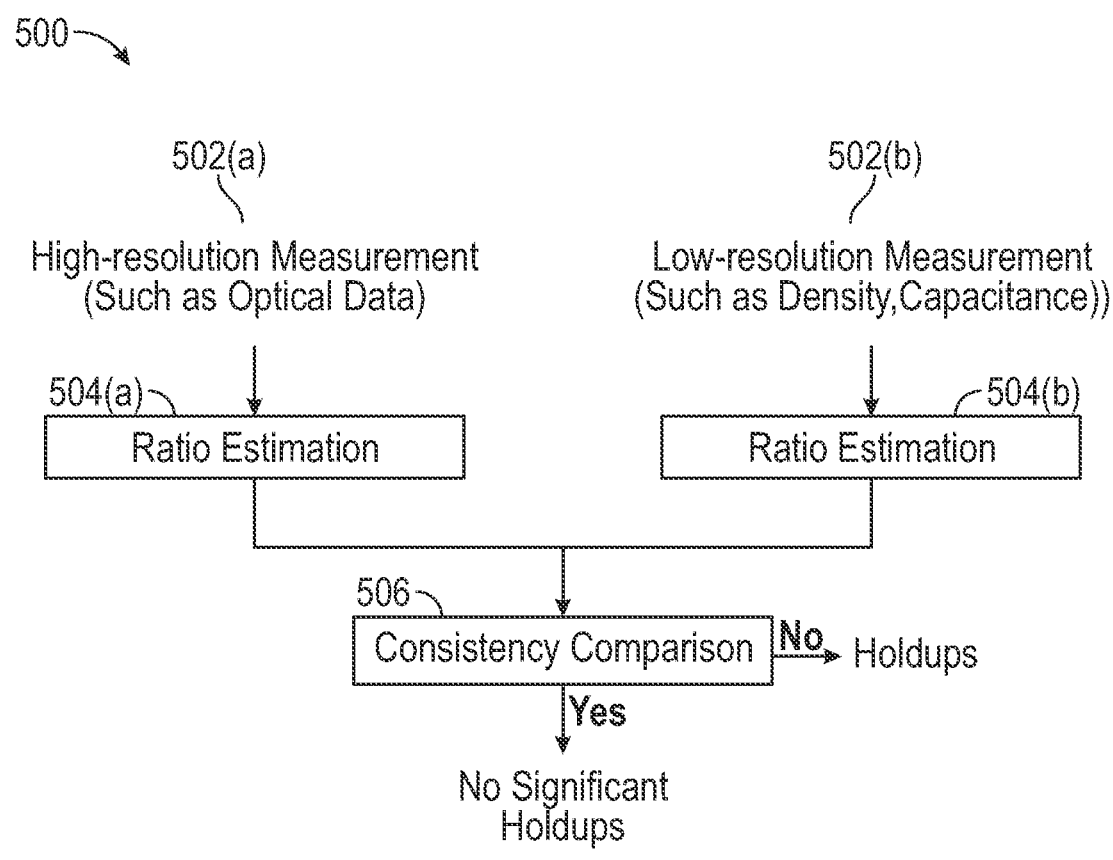
FIG. 5 is a flow chart of a workflow for holdup monitoring, according to certain illustrative methods of the present disclosure.

FIG. 5 is a flow chart of a workflow for holdup monitoring, according to certain illustrative methods of the present disclosure. In this shown example, optical data is used as the high-spatial resolution measurement (obtained using high spatial resolution sensors), while density data is used as the low-resolution data (obtained using low spatial resolution sensors). In blocks 502(a) and (b) of method 500, high- and low-resolution measurements of the fluid sample are obtained using a sampling tool positioned along a wellbore. The high-spatial resolution measurements may be, for example, an optical, infrared or laser measurement. The low-resolution measurements may be, for example, a density or capacitance measurement. At blocks 504(a) and (b), water ratios of the high- and low-spatial resolution measurements are calculated. In this example, the water ratio refers to the amount of mud water in the sample vs. the total fluid. These water ratios may be calculated in a variety of ways including, for example, based upon a threshold of the density or capacitance measurement. Here, for example, with the case of water ratio estimation from density, a user may set a threshold, for example 0.7. If the sampled density is lower than 0.7, it is formation fluid, while if the sampled density is higher than 0.7, it is mud-fluid (water). Thus, the mud-fluid ratio or formation fluid ratio is calculated by the numbers of mud-fluid samples and formation fluid samples in a time window.

In other examples, a clustering method may be applied to the optical measurement in order to calculate the water ratio. An example of this clustering method is described in co-pending PCT Application No. PCT/US2021/054428, entitled "Multi-Phase Fluid Identification For Subsurface Sensor Measurement," naming Chen et al. as inventors, assigned to Halliburton Energy Services, Inc., the disclosure of which is hereby incorporated by reference in its entirety.

In yet other examples, the mud-water ratio or formation fluid ratio may be used (note the water ratio is the mud fluid ratio when the mud is water-based mud). As with the water ratio example above, the formation fluid ratio may also be used for the holdup monitoring.

At block 506 of method 500, the consistency of the water ratios of the high- and low-resolution measurements are compared to one another. In this step, the correlation consistency of the measurements is compared. If the system determines the ratio estimated from the high-resolution measurement is higher than the ratio estimated from low-resolution measurement, a fluid holdup is identified. The ratio may be, for example, a mud-water ratio or a formation fluid ratio. For example, if the deviation between the high- and low-resolution measurements exceeds a given threshold (e.g., 0.7), then a fluid holdup is identified. In the examples using the formation fluid ratio instead of mud water ratio, the holdups may be identified when the ratio of the high-resolution measurement is lower than the ratio of the low-resolution measurement by a factor of, for example, 5% or more. Thereafter, the identified holdups can be flushed from the sampling tool. If, however, at block 506 the system determines the ratio of the high-resolution measurement corresponds (i.e., is within a defined deviation range of, e.g., 0-5%) to the ratio of the low-resolution measurement, no holdup is identified.

Figure 6:
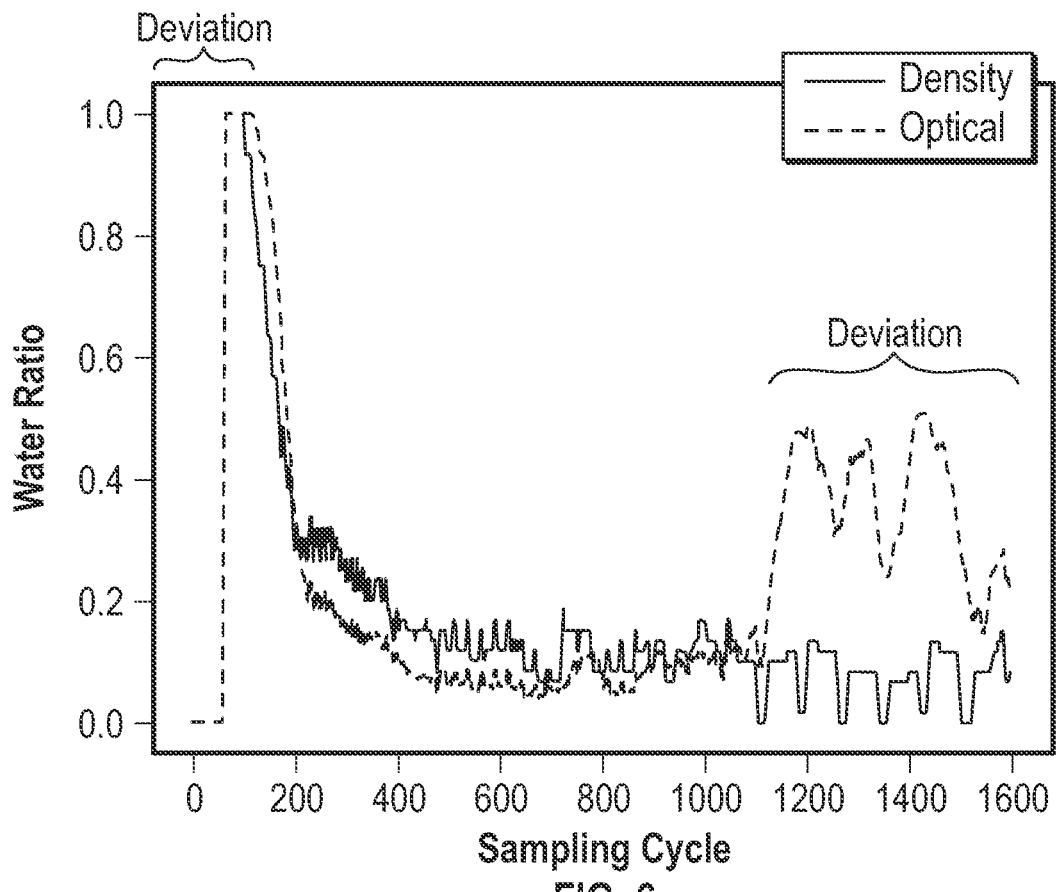
FIG. 6 is a graph illustrating an example of holdup monitoring based on optical measurement and density measurement of the data in FIG. 1.

FIG. 6 is a graph illustrating an example of holdup monitoring based on optical measurement and density measurement of the data in FIG. 4. The water ratio estimations of the two physical measurements (high- and low-resolution measurements) are consistent until 1100 sampling cycles (11000 seconds), where a deviation can then be seen. In this example, the low pump rates began at 11,000 seconds. From that time (low pump rates began), there were mud water holdups on the pipe, and application of the present disclosure in this case clearly shows the inconsistency (i.e., deviation) of the water ratio estimations (thereby identifying the holdups along the pipes). The analysis of FIG. 6 shows the mud fluid ratio estimation based on optical data, matches well with the one based on density measurements until the pump changed to a low pumping rate at 1100 sampling circles. After that, the optical data becomes unreliable, and deviation of the two mud fluid ratios can be seen around 1100 sampling cycles. Thereafter, around 1600 sampling cycles, a flushing procedure was initiated which once again brought the two measurements back in correlation with one another.

In the foregoing examples, the fluid holdups are monitored by directly comparing the real time graphs of the estimated water ratios. In alternate embodiments, however, there are a variety of similarity measures or distance measures between the two water ratios that can be applied as indicating indexes (indicators) for holdups. However, all of these alternative methods are based on the discovery of multi-physical measurements (i.e., use of high- and low-resolution measurements) disclosed herein.

Accordingly, illustrative embodiments of the present disclosure provide real time monitoring of the holdups that provide additional information to evaluate the reliability of the subsurface measurements. Moreover, guided by the holdup monitoring information, field engineers can start the mechanical flushing procedure earlier to save hours of time spent on unnecessary flushing procedures.

Figure 7:
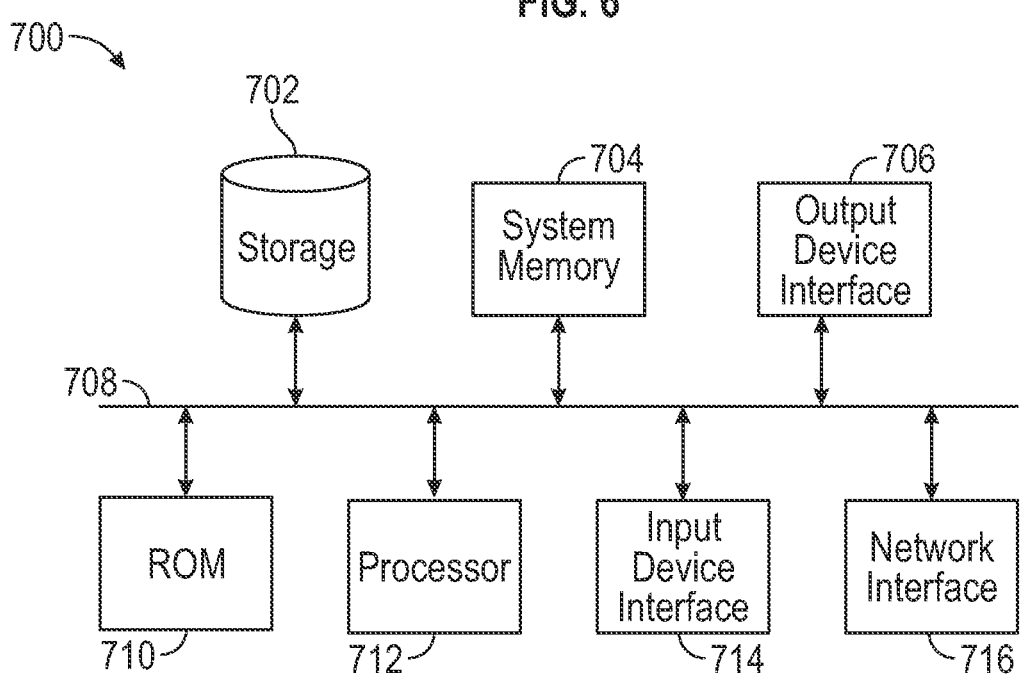
FIG. 7 is a block diagram of an exemplary computer system in which embodiments of the present disclosure may be implemented.

FIG. 7 is a block diagram of an exemplary computer system 700 in which embodiments of the present disclosure may be implemented. System 700 can be a computer, phone, PDA, or any other type of electronic device. Such an electronic device includes various types of computer readable media and interfaces for various other types of computer readable media. As shown in FIG. 7, system 700 includes a permanent storage device 702, a system memory 704, an output device interface 706, a system communications bus 708, a read-only memory (ROM) 710, processing unit(s) 712, an input device interface 714, and a network interface 716.

Bus 708 collectively represents all system, peripheral, and chipset buses that communicatively connect the numerous internal devices of system 700. For instance, bus 708 communicatively connects processing unit(s) 712 with ROM 710, system memory 704, and permanent storage device 702. From these various memory units, processing unit(s) 712 retrieves instructions to execute and data to process in order to execute the processes of the subject disclosure. The processing unit(s) can be a single processor or a multi-core processor in different implementations.

ROM 710 stores static data and instructions that are needed by processing unit(s) 712 and other modules of system 700. Permanent storage device 702, on the other hand, is a read-and-write memory device. This device is a non-volatile memory unit that stores instructions and data even when system 700 is off. Some implementations of the subject disclosure use a mass-storage device (such as a magnetic or optical disk and its corresponding disk drive) as permanent storage device 702.

Other implementations use a removable storage device (such as a floppy disk, flash drive, and its corresponding disk drive) as permanent storage device 702. Like permanent storage device 702, system memory 704 is a read-and-write memory device. However, unlike storage device 702, system memory 704 is a volatile read-and-write memory, such a random access memory. System memory 704 stores some of the instructions and data that the processor needs at runtime. In some implementations, the processes of the subject disclosure are stored in system memory 704, permanent storage device 702, and/or ROM 610. For example, the various memory units include instructions for computer aided pipe string design based on existing string designs in accordance with some implementations. From these various memory units, processing unit(s) 712 retrieves instructions to execute and data to process in order to execute the processes of some implementations.

Bus 708 also connects to input and output device interfaces 714 and 706. Input device interface 714 enables the user to communicate information and select commands to the system 700. Input devices used with input device interface 714 include, for example, alphanumeric, QWERTY, or T9 keyboards, microphones, and pointing devices (also called "cursor control devices"). Output device interfaces 706 enables, for example, the display of images generated by the system 700. Output devices used with output device interface 706 include, for example, printers and display devices, such as cathode ray tubes (CRT) or liquid crystal displays (LCD). Some implementations include devices such as a touchscreen that functions as both input and output devices. It should be appreciated that embodiments of the present disclosure may be implemented using a computer including any of various types of input and output devices for enabling interaction with a user. Such interaction may include feedback to or from the user in different forms of sensory feedback including, but not limited to, visual feedback, auditory feedback, or tactile feedback. Further, input from the user can be received in any form including, but not limited to, acoustic, speech, or tactile input. Additionally, interaction with the user may include transmitting and receiving different types of information, e.g., in the form of documents, to and from the user via the above-described interfaces.

Also, as shown in FIG. 7, bus 708 also couples system 700 to a public or private network (not shown) or combination of networks through a network interface 716. Such a network may include, for example, a local area network ("LAN"), such as an Intranet, or a wide area network ("WAN"), such as the Internet. Any or all components of system 700 can be used in conjunction with the subject disclosure.

These functions described above can be implemented in digital electronic circuitry, in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself. Accordingly, the steps of processes described above may be implemented using system 600 or any computer system having processing circuitry or a computer program product including instructions stored therein, which, when executed by at least one processor, causes the processor to perform functions relating to these methods.

It is understood that any specific order or hierarchy of steps in the processes disclosed is an illustration of exemplary approaches. Based upon design preferences, it is understood that the specific order or hierarchy of steps in the processes may be rearranged, or that all illustrated steps be performed. Some of the steps may be performed simultaneously. For example, in certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Embodiments and methods of the present disclosure described herein further relate to any one or more of the following paragraphs:

1. A method to identify fluid holdups during downhole fluid sampling operations, the method comprising obtaining, using a sampling tool positioned within a wellbore, one or more first fluid measurements having a first spatial resolution; obtaining, using the sampling tool, one or more second fluid measurements having a second spatial resolution lower than the first spatial resolution; calculating a first ratio of the first fluid measurements; calculating a second ratio of the second fluid measurements; comparing the first ratio to the second ratio; and based upon the comparison, identifying fluid holdups within the sampling tool.
2. The method as defined in paragraph 1, wherein the first fluid measurement is an optical measurement, infrared measurement or laser measurement.
3. The method as defined in paragraph 1 or 2, wherein the second fluid measurement is a density measurement or capacitance measurement.
4. The method as defined in any of paragraphs 1-3, wherein the first and second ratios are water ratios of the first and second fluid measurements.
5. The method as defined in any of paragraphs 1-4, wherein the first and second ratios are mud ratios of the first and second fluid measurements.
6. The method as defined in any of paragraphs 1-5, wherein the first and second ratios are formation fluid ratios of the first and second fluid measurements.
7. The method as defined in any of paragraphs 1-6, further comprising flushing the fluid holdups out of the sampling tool.
8. A system to identify fluid holdups during downhole fluid sampling operations, the system comprising a fluid sampling tool comprising: a first spatial resolution sensor; and a second spatial resolution sensor having a spatial resolution lower than the first spatial resolution sensor; and processing circuitry to perform operations comprising: obtaining, using the first spatial resolution sensor, one or more first fluid measurements; obtaining, using the second spatial resolution sensor, one or more second fluid measurements; calculating a first ratio of the first fluid measurements; calculating a second ratio of the second fluid measurements; comparing the first ratio to the second ratio; and based upon the comparison, identifying fluid holdups within the sampling tool.

9. The system as defined in paragraph 8, wherein the first spatial resolution sensor is an optical, infrared or laser sensor.

10. The system as defined in paragraphs 8 or 9, wherein the second spatial resolution sensor is a density sensor or capacitance sensor.

11. The system as defined in any of paragraphs 8-10, wherein the first and second ratios are water ratios of the first and second fluid measurements.

12. The system as defined in any of paragraphs 8-11, wherein the first and second ratios are mud ratios of the first and second fluid measurements.

13. The system as defined in any of paragraphs 8-12, wherein the first and second ratios are formation fluid ratios of the first and second fluid measurements.

14. The system as defined in any of paragraphs 8-13, further comprising flushing the fluid holdups out of the sampling tool.

Furthermore, the exemplary methodologies described herein may be implemented by a system including processing circuitry or a non-transitory computer program product including instructions which, when executed by at least one processor, causes the processor to perform any of the methodology described herein.

Although various embodiments and methodologies have been shown and described, the invention is not limited to such embodiments and methodologies and will be understood to include all modifications and variations as would be apparent to one skilled in the art. Therefore, it should be understood that the invention is not intended to be limited to the particular forms disclosed. Rather, the intention is to cover all modifications, equivalents and alternatives falling within the spirit and scope of the invention as defined by the appended claims.

What is claimed is:

1. A method to identify fluid holdups during downhole fluid sampling operations, the method comprising:
   obtaining, using a sampling tool positioned within a wellbore, one or more fluid measurements using at least one sensor having a first set of spatial resolution, wherein the at least one sensor is selected from the group of sensors consisting of an optical spectroscopy, index of refraction, fluorescence, a laser, and any combination thereof;
   obtaining, using the sampling tool, one or more fluid measurements using at least one sensor having a second set of spatial resolution, wherein the at least one sensor is selected from the group of sensors consisting of a density, capacitance, dielectric spectroscopy, viscosity sensor, and any combination thereof, wherein the second set of spatial resolution is lower than the first set of spatial resolution;
   calculating a first fluid ratio comprising a water ratio, an oil ratio, or a gas ratio using the at least one sensor having the first set of spatial resolution;
   calculating a second fluid ratio using the at least one sensor having the second set of spatial resolution; and
   identifying fluid holdup within the sampling tool when the differences between the two fluid ratios are higher than a limit or a similarity of the two fluid ratios are lower than a limit.

2. The method as defined in claim 1, wherein the first and second ratios are mud ratios of the first and second fluid measurements.

3. The method as defined in claim 1, wherein the first and second ratios are formation fluid ratios of the first and second fluid measurements.

4. The method as defined in claim 1, further comprising flushing the fluid holdups out of the sampling tool.

5. A system to identify fluid holdups during downhole fluid sampling operations, the system comprising:
   a fluid sampling tool comprising:
      a first spatial resolution sensor, wherein the first spatial resolution sensor is an optical, infrared or laser sensor; and
      a second spatial resolution sensor having a spatial resolution lower than the first spatial resolution sensor, wherein the second spatial resolution sensor is a density, dielectric, viscosity, or capacitance sensor; and
   processing circuitry to perform operations comprising:
      obtaining, using the first spatial resolution sensor, one or more fluid measurements;
      obtaining, using the second spatial resolution sensor, one or more fluid measurements;
      calculating a first fluid ratio comprising a water ratio, an oil ratio, or a gas ratio using the first spatial resolution sensor;
      calculating a second fluid ratio using the second spatial resolution sensor; and
      identifying fluid holdup within the fluid sampling tool when the differences between the two fluid ratios are higher than a limit or a similarity of the two fluid ratios are lower than a limit.

6. The system as defined in claim 5, wherein the first and second ratios are mud ratios of the first and second fluid measurements.

7. The system as defined in claim 5, wherein the first and second ratios are formation fluid ratios of the first and second fluid measurements.

8. The system as defined in claim 5, further comprising flushing the fluid holdups out of the sampling tool.

9. A non-transitory computer program product including instruction which, when executed by at least one processor, causes the processor to a method comprising:
   obtaining, using a sampling tool positioned within a wellbore, one or more fluid measurements using an optical spectroscopy, index of refraction, fluorescence, or a laser sensor;
   obtaining, using the sampling tool, one or more fluid measurements using a density, capacitance, dielectric spectroscopy, or viscosity sensor, wherein the optical spectroscopy, index of refraction, fluorescence, or laser sensor has a higher spatial resolution than the density, capacitance, dielectric spectroscopy, or viscosity sensor;
   calculating a first fluid ratio comprising a water ratio, an oil ratio, or a gas ratio using the optical spectroscopy, index of refraction, fluorescence, or laser sensor;
   calculating a second fluid ratio using the density, capacitance, dielectric spectroscopy, or viscosity sensor; and identifying fluid holdup within the sampling tool when the differences between the two fluid ratios are higher than a limit or a similarity of the two fluid ratios are lower than a limit.

10. The computer program product as defined in claim 9, wherein the first and second ratios are mud ratios of the first and second fluid measurements.

11. The computer program product as defined in claim 9, wherein the first and second ratios are formation fluid ratios of the first and second fluid measurements.

12. The computer program as defined in claim 9, further comprising flushing the fluid holdups out of the sampling tool.

\* \* \* \* \*